(12) United States Patent
Zare et al.

(10) Patent No.: US 9,713,702 B2
(45) Date of Patent: Jul. 25, 2017

(54) METHODS OF ELECTRIC FIELD INDUCED DELIVERY OF COMPOUNDS, COMPOSITIONS USED IN DELIVERY, AND SYSTEMS OF DELIVERY

(75) Inventors: Richard N. Zare, Stanford, CA (US); Jun Ge, Palo Alto, CA (US)

(73) Assignee: The Board of Trustee of the Leland Stanford Junior University, Palo Alto (*) Notice: Subject to any disclaimer, the term of this patent is extended or adjusted under 35 U.S.C. 154(b) by 1217 days.

(21) Appl. No.: 13/415,885

(22) Filed: Mar. 9, 2012

(65) Prior Publication Data
US 2012/0238943 A1 Sep. 20, 2012

Related U.S. Application Data

(60) Provisional application No. 61/452,192, filed on Mar. 14, 2011.

(51) Int. Cl.
| | | |
|---|---|---|
| *A61K 9/51* | (2006.01) | |
| *A61M 37/00* | (2006.01) | |
| *A61K 9/00* | (2006.01) | |
| *A61K 9/06* | (2006.01) | |

(52) U.S. Cl.
CPC .......... *A61M 37/00* (2013.01); *A61K 9/0009* (2013.01); *A61K 9/0024* (2013.01); *A61K 9/06* (2013.01); *A61K 9/5138* (2013.01); *A61M 2037/0007* (2013.01)

(58) Field of Classification Search
CPC .. A61K 9/0009; A61K 9/0024; A61K 9/5138; A61K 9/06; A61K 9/51; A61K 9/10; A61K 47/00; A61M 37/00; A61M 2037/0007
See application file for complete search history.

(56) References Cited

U.S. PATENT DOCUMENTS

| | | | |
|---|---|---|---|
| 4,585,652 A | | 4/1986 | Miller et al. |
| 5,565,215 A | * | 10/1996 | Gref ..................... A61K 9/0019 424/451 |
| 7,437,189 B2 | * | 10/2008 | Matsumura ........... A61N 1/306 604/21 |
| 8,666,471 B2 | * | 3/2014 | Rogers et al. ................ 600/377 |
| 2008/0097280 A1 | * | 4/2008 | Martin ................ A61K 9/0009 604/21 |
| 2008/0233200 A1 | * | 9/2008 | Sung .................... A61K 9/0019 424/499 |
| 2009/0155374 A1 | * | 6/2009 | Sung .................... A61K 9/4891 514/1.1 |
| 2011/0021899 A1 | | 1/2011 | Arps et al. |

OTHER PUBLICATIONS

Lin et al., "PEG hydrogels for the controlled release of biomolecules in regenerative medicine", Pharmaceutical Research, vol. 26, No. 3, pp. 631-643, Mar. 2009.*

(Continued)

*Primary Examiner* — Nathan R Price
*Assistant Examiner* — Melissa A Snyder
(74) *Attorney, Agent, or Firm* — Thomas|Horstemeyer, LLP

(57) ABSTRACT

In accordance with the purpose(s) of the present disclosure, as embodied and broadly described herein, embodiments of the present disclosure, in one aspect, relate to methods of delivering a compound, a composition, and the like.

16 Claims, 9 Drawing Sheets

(56) References Cited

OTHER PUBLICATIONS

The International Search Report and Written Opinion dated Sep. 19, 2012.

Lin, et al., "PEF Hydrogels for the Controlled Release of Biomolecules in Regenerative Medicine," Pharmaceutical Research, vol. 26, No. 3, pp. 631-643, Mar. 2009.

Guiiseppi-Elie, "Electroconductive Hydrogels: Synthesis, Characterization and Biomedical Applications," Biomaterials, vol. 31, pp. 2701-2716, Jan. 8, 2010.

Brahim, et al., "Electroconductive Hydrogels: Electric and Electrochemical Properties of Polypyrole-poly (HEMA) Composites," Electroanalysis, vol. 17, No. 7, pp. 556-570, 2005.

Svirskis, et al., "Electrochemically Controlled Drug Delivery Based on Intrinsically Conducting Polymers" Journal of Controlled Release, vol. 146, pp. 6-15, 2010.

Wadhwa, et al., "Electrochemcially Controlled Release of Dexamethasone from Conducting Polymer Polypyrole Coated Electrode," Journal of Controlled Release, vol. 110, pp. 531-541, 2006.

You et al., "Conductive, Physiologically Responsive Hydrogels," Langmuir, vol. 26, No. 7, pp. 4607-4612, 2010.

Ge, et al., "Drug Release from Electric-Field-Responsive Nanoparticles," ACS Nano, vol. 6, No. 1, pp. 227-233, 2012.

Guimard NK, Gomez N, Schmidt CE. Conducting polymers in biomedical engineering. Prog. Polym. Sci. 32 (2007) 876-921.

Rao JP, Geckeler KE. Polymer nanoparticles:Preparation techniques and size-control parameters. Prog. Polym. Sci. vol. 36, Issue 7, Jul. 2011, pp. 887-913.

Kim SW, Cho HG, Park CR. Fabrication of Unagglomerated Polypyrrole Nanospheres with Controlled Sizes From a Surfactant-Free Emulsion System. Langmuir 2009, 25(16), 9030-9036.

Svirkis D, Wright BE, Travas-Sedjic J, Rodgers A, Garg S. Development of a Controlled Release System for Risperidone Using Polypyrrole: Mechanistic Studies. Electroanalysis 2010, 22, No. 4, 439-444.

\* cited by examiner

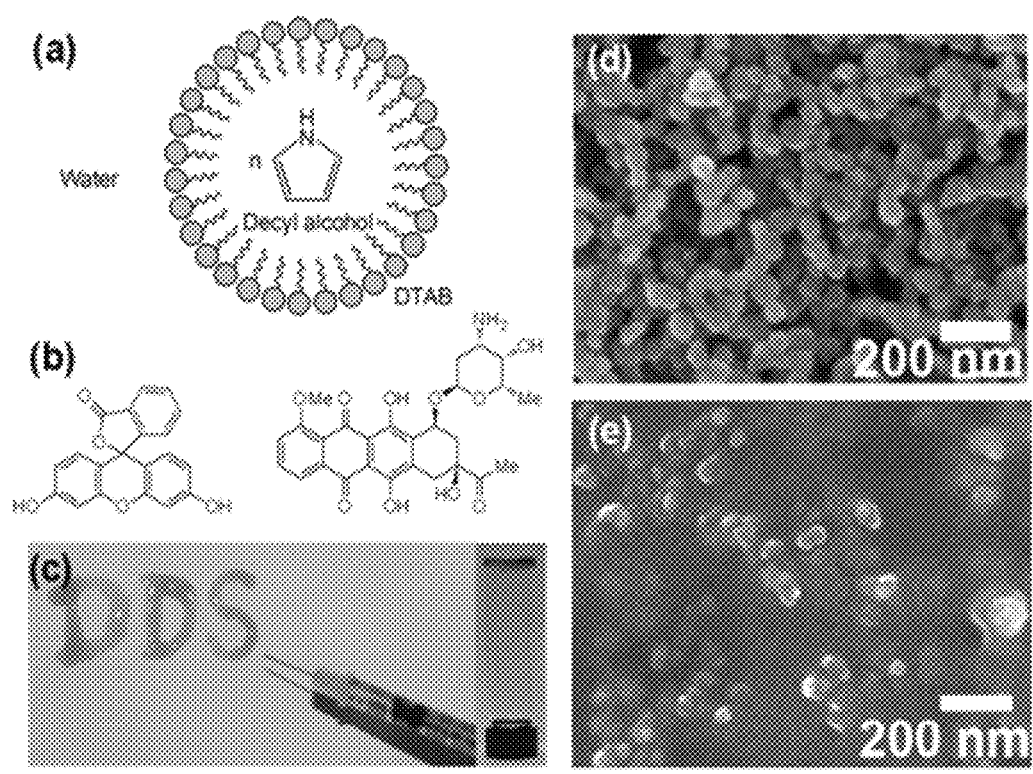
FIG. 1.1

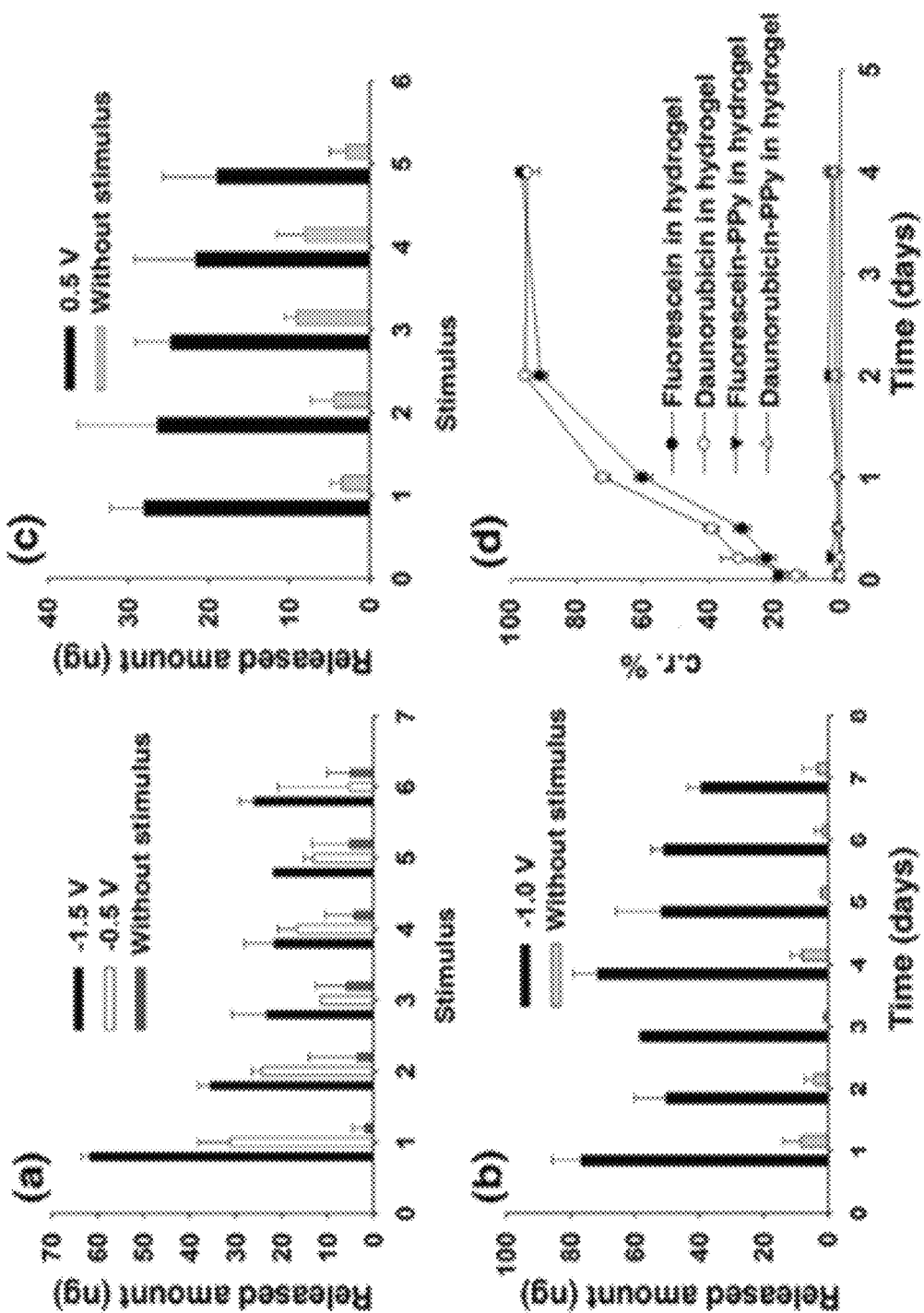
FIG. 1.2

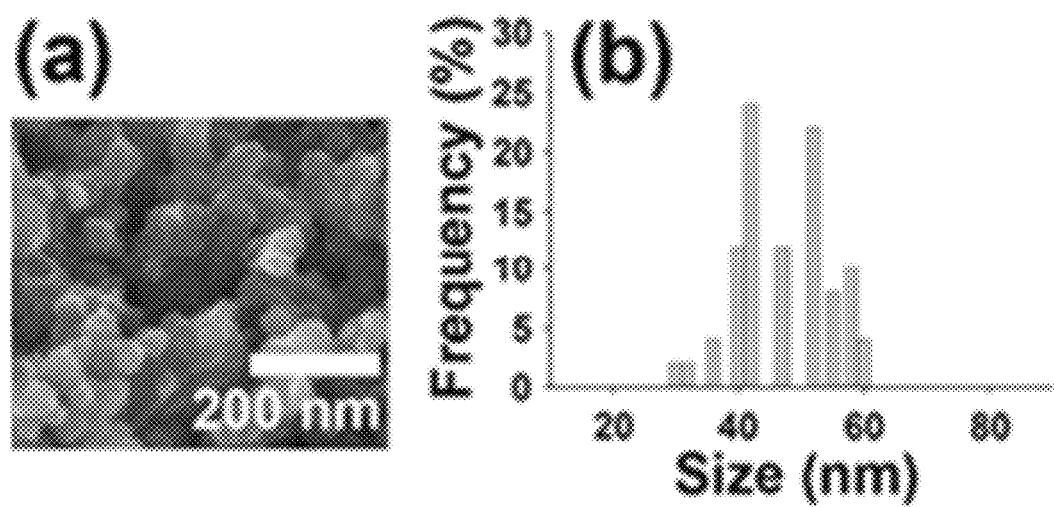
FIG. 1.3

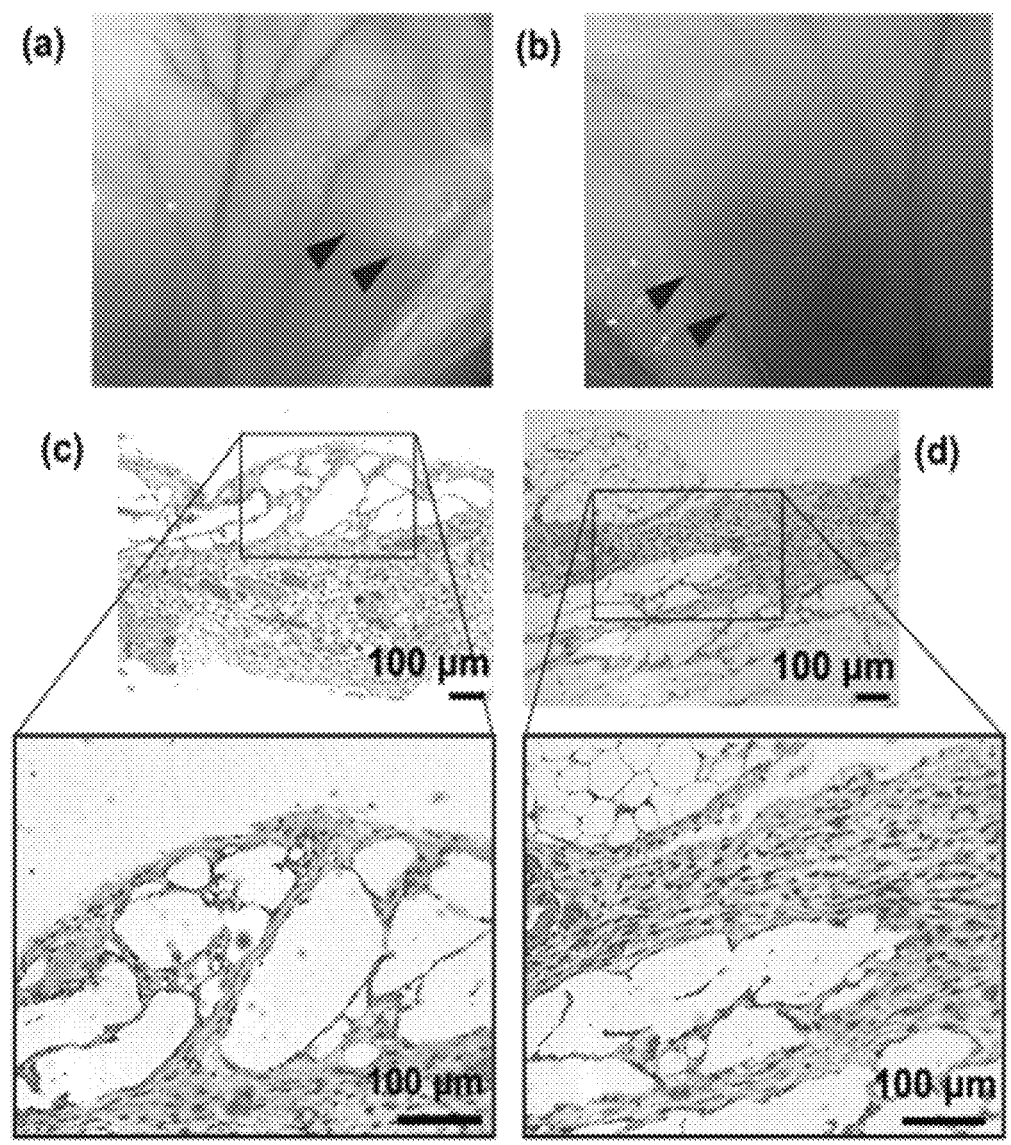
FIG. 1.4

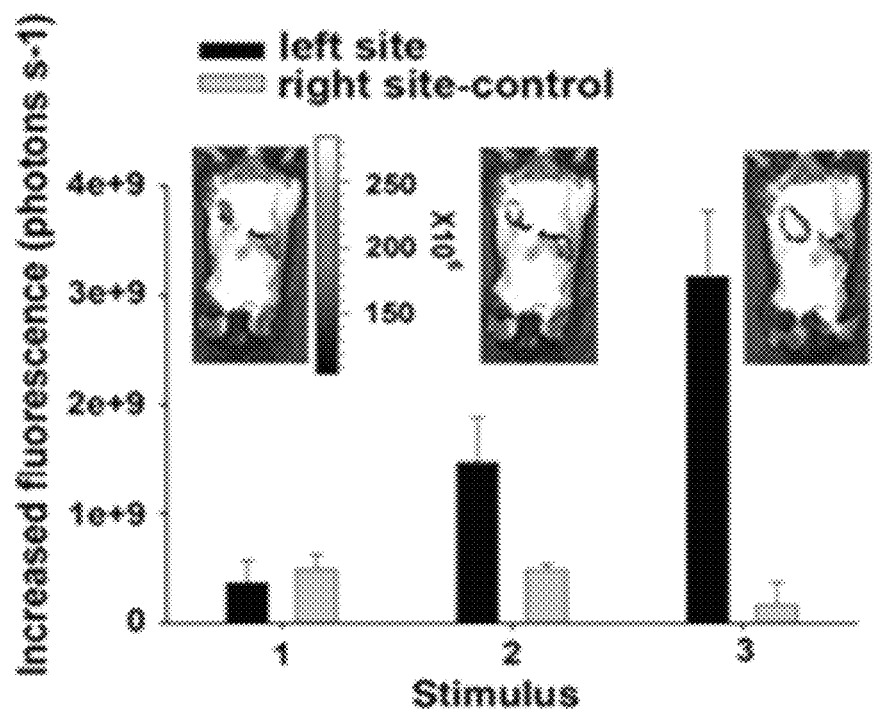
FIG. 1.5
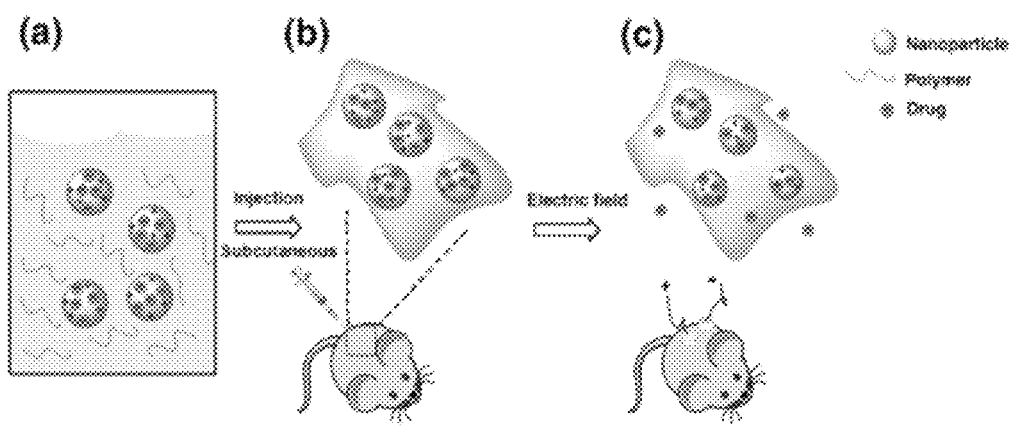
FIG. 1.6

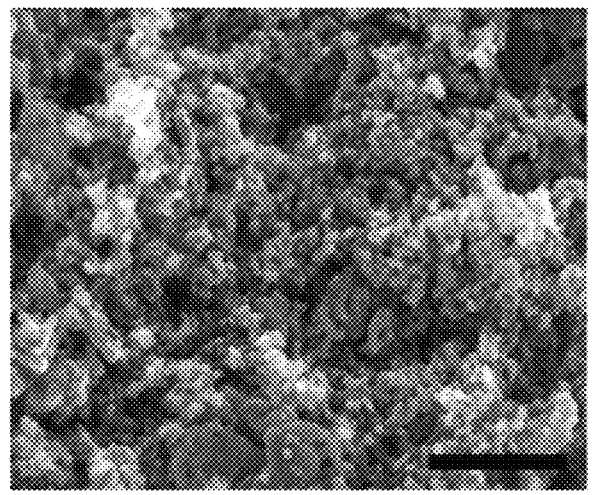
FIG. 2.1
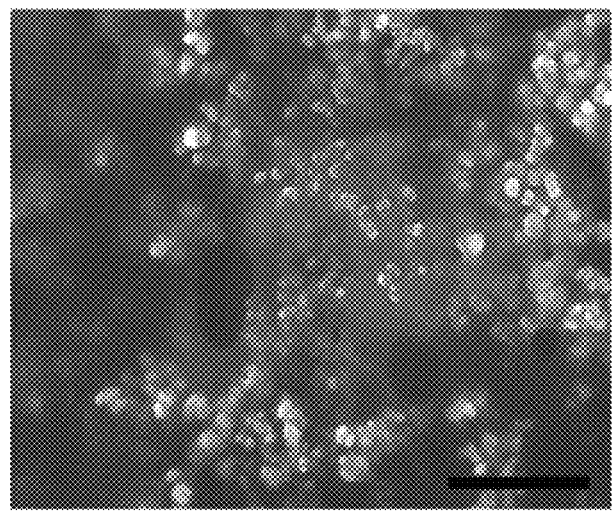
FIG. 2.2

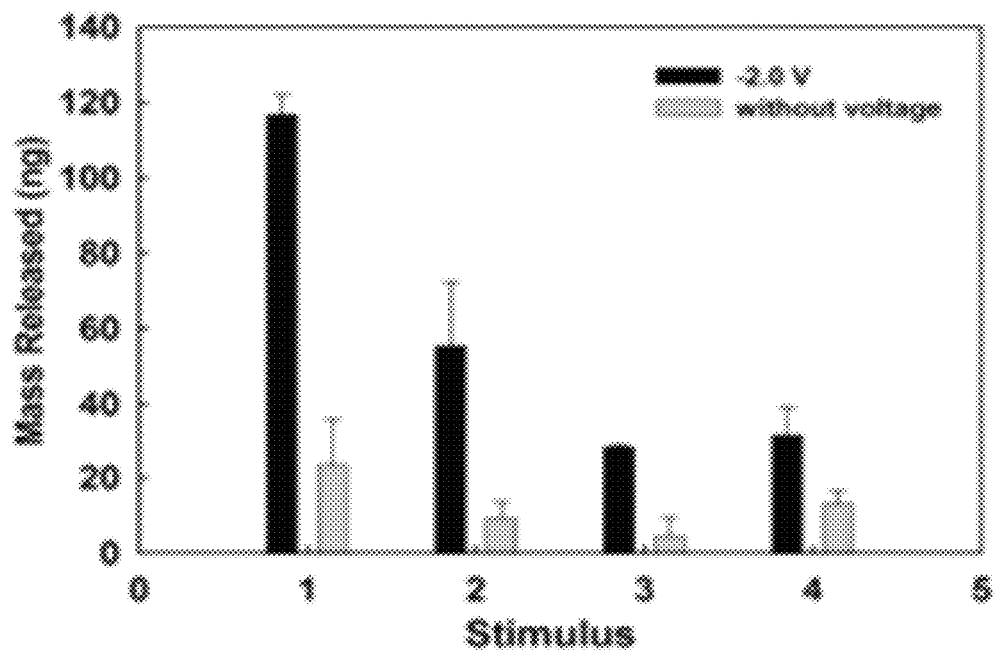
FIG. 2.3
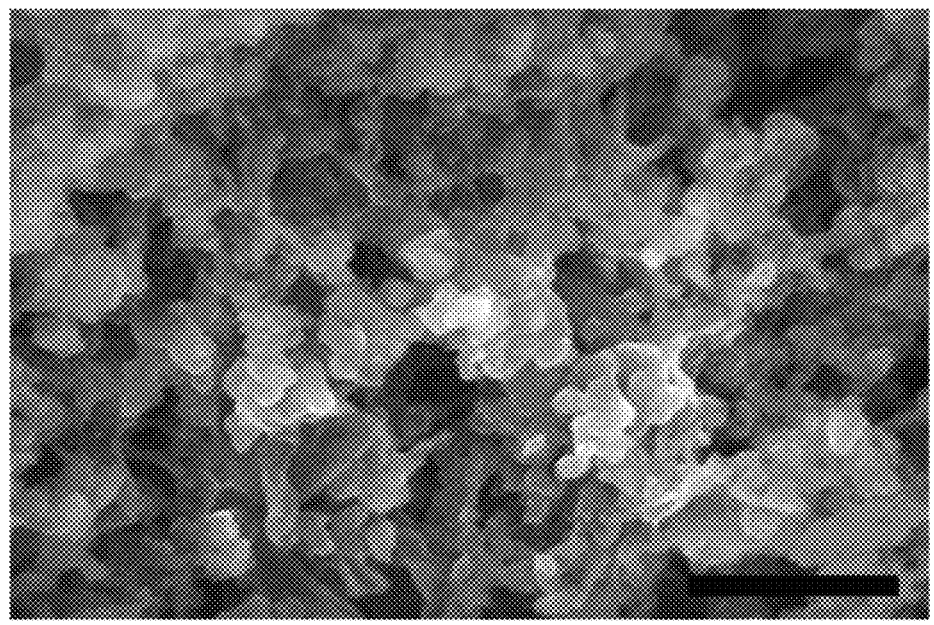
FIG. 3.1

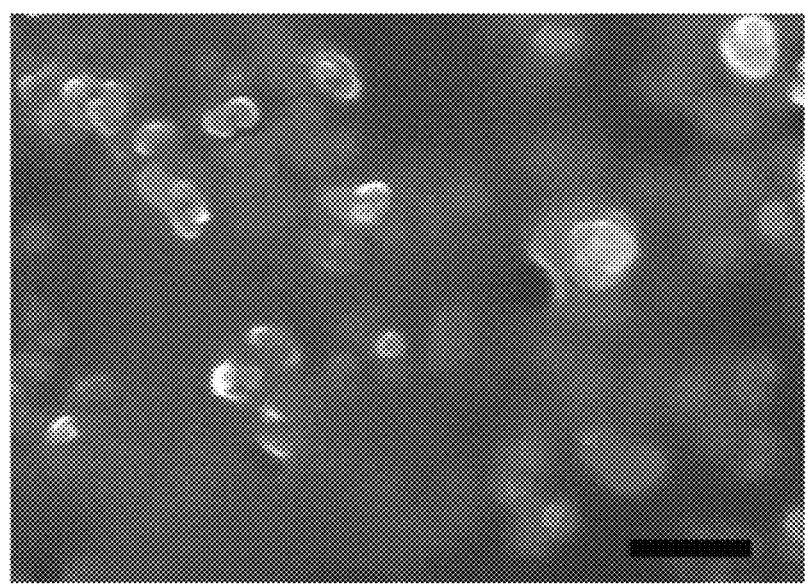
FIG. 3.2
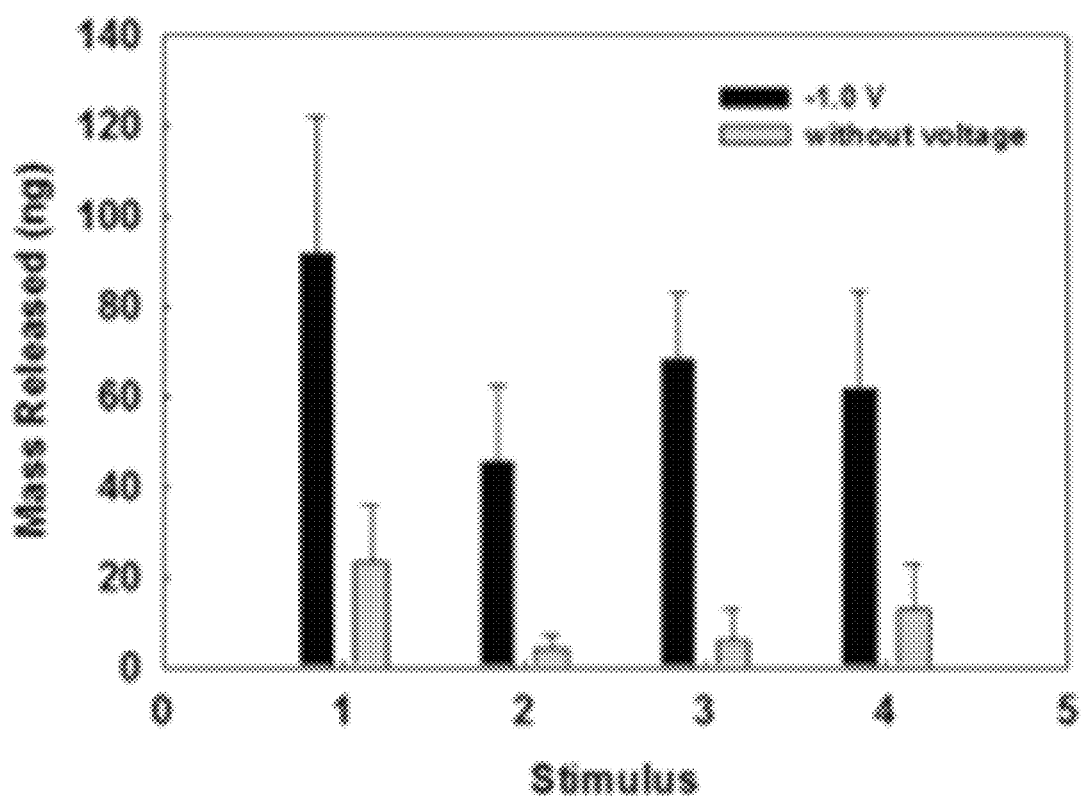
FIG. 3.3

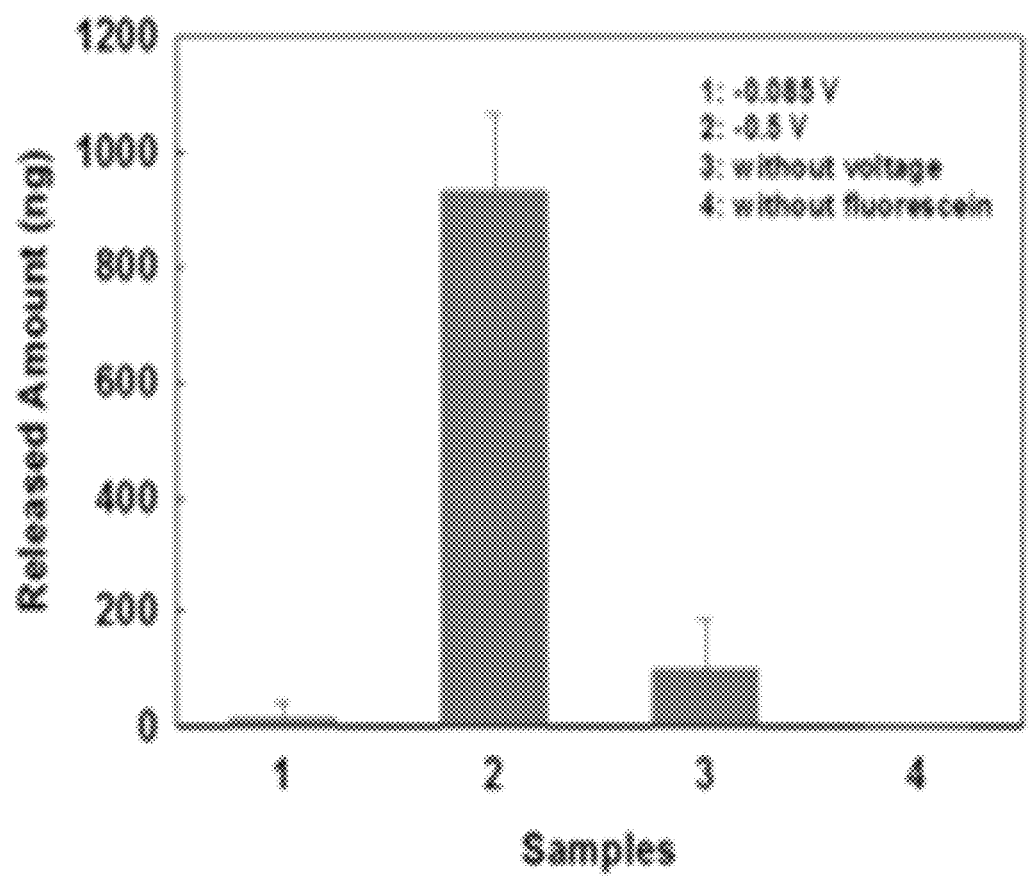
FIG. 4.1

METHODS OF ELECTRIC FIELD INDUCED DELIVERY OF COMPOUNDS, COMPOSITIONS USED IN DELIVERY, AND SYSTEMS OF DELIVERY

CROSS-REFERENCE TO RELATED APPLICATION

This application claims priority to U.S. provisional application entitled "METHODS OF ELECTRIC FIELD INDUCED DELIVERY OF COMPOUNDS, COMPOSITIONS USED IN DELIVERY, AND SYSTEMS OF DELIVERY," having Ser. No. 61/452,192, filed on Mar. 14, 2011, which is entirely incorporated herein by reference.

STATEMENT REGARDING FEDERALLY SPONSORED RESEARCH OR DEVELOPMENT

This invention(s) was made with government support under Grant No.: 0827806, which was awarded by the National Science Foundation. The government has certain rights in the invention(s).

BACKGROUND

One of the most challenging topics facing the prospect of realized drug delivery via nanomaterials is the controlled release of a specific drug as desired. This critical "triggering" of a drug manifests itself in a plethora of ways: spatially, temporally, and dosage precision. To cause release, many different approaches have been undertaken; stimuli-responsive materials which respond in the presence of heat, pH, light, enzymes, magnetic field, or electric field can be used.

SUMMARY

In accordance with the purpose(s) of the present disclosure, as embodied and broadly described herein, embodiments of the present disclosure, in one aspect, relate to methods of delivering a compound, a composition, and the like.

In an embodiment, one method of delivering a composition, among others, of includes: disposing a composition including a conductive polymer nanoparticle into an area of a subject, wherein the conductive polymer nanoparticle includes a conductive polymer encapsulating a compound, wherein a charge is associated with the compound; and applying an electric field to the area for a period of time, wherein the electric field causes the controllable release of the compound from the conductive polymer nanoparticle.

In an embodiment, one composition, among others, of includes: a conductive polymer nanoparticle that includes a conductive polymer encapsulating a compound, wherein a charge is associated with the compound.

BRIEF DESCRIPTION OF THE DRAWINGS

Many aspects of the disclosed devices and methods can be better understood with reference to the following drawings. The components in the drawings are not necessarily to scale, emphasis instead being placed upon clearly illustrating the relevant principles. Moreover, in the drawings, like reference numerals designate corresponding parts throughout the several views.

FIG. 1.1: (*a*) Chemical synthesis of polypyrrole nanoparticles. (*b*) Chemical structures of fluorescein (left) and daunorubicin (right). (*c*) Photograph showing the sol-gel transition of the injectable conductive hydrogel. (DDS: drug delivery system) (*d*) SEM image of fluorescein-encapsulated polypyrrole nanoparticles. (*e*) SEM image of air-dried hydrogel containing polypyrrole nanoparticles.

FIG. 1.2: Electric field induced release from the conductive hydrogel. (*a*) Released amount of fluorescein in PBS (pH 7.2) following an applied voltage (−0.5 or −1.5 V) duration of 10 s, repeated every five minutes. (*b*) Released amount of fluorescein in PBS (pH 7.2) following an applied voltage duration of 20 s, repeated every day. (*c*) Released amount of daunorubicin in PBS (pH 7.2) following an applied voltage (0.5 V) duration of 10 s, repeated every five minutes. (*d*) Cumulative release (c.r.) of drugs from hydrogel and from PPy nanoparticles in hydrogel without applying voltage.

FIG. 1.3: (*a*) SEM images of fluorescein-encapsulated polypyrrole nanoparticles after release. (*b*) Histograms showing particle size distributions calculated from SEM images.

FIGS. 1.4: (*a*) and (*b*) are the photographs of in situ formed conductive hydrogels containing 1 wt % of PPy NPs after a subcutaneous injection in FVB mice. The hydrogel formed subcutaneously in the mouse and showed a spherical to ovoid shape after 1 week (a) and 2 weeks (b) healing. The gel was removed from the mouse on week 1 and 2. Black arrows indicated the implants. (*c*) and (*d*) are H&E stained images of the conductive hydrogels after subcutaneous implantation in an FVB mouse at 1 week (c) and 2 weeks (d). H&E stain cells could be observed in the hydrogel area.

FIG. 1.5: In vivo fluorescent images after applying an electric field of −1.5 V/cm to the implanted conductive hydrogels. The unit is photons per second. The unit of the scale on the right of the mouse image is photons per steradian per second. (1) Before applying voltage. (2) and (3) Apply voltage on the left injection site for 40 seconds; the right injection site is control without applying voltage.

FIG. 1.6: A general scheme for the application of this system. (*a*) The nanoparticle-polymer solution is (*b*) subcutaneously injected into a mouse; followed by (*c*) application of a DC electric field to induce release of the drug cargo inside the nanoparticles.

FIG. 2.1: SEM images of D-luciferin-encapsulated PPy nanoparticles. (Scale bar: 1 µm)

FIG. 2.2: SEM images of the conductive hydrogel with luciferin-encapsulated PPy nanoparticles. (Scale bar: 1 µm)

FIG. 2.3: Released amount of luciferin in phosphate buffered saline (PBS pH 7.2), with applying a voltage stimulus for 10 s to the conductive hydrogels in every 5 min.

FIG. 3.1: SEM images of fluorescein-encapsulated PEDOT nanoparticles. (Scale bar: 500 nm)

FIG. 3.2: SEM images of the conductive hydrogel with fluorescein-encapsulated PEDOT nanoparticles. (Scale bar: 200 nm)

FIG. 3.3: Released amount of fluorescein in phosphate buffered saline (PBS pH 7.4), with applying a voltage stimulus for 10 s to the conductive hydrogels in every 5 min.

FIG. 4.1: A voltage of −0.085 V/cm (sample 1) is not enough to trigger the release of encapsulated fluorescein in conductive nanoparticles, while a voltage of −0.5 V/cm (sample 2) can trigger the release.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, biochemistry, biology, molecular biology, and the like, which are within the skill of the art.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a compound" includes a plurality of compounds. In this specification and in the claims that follow, reference will be made to a number of terms that shall be defined to have the following meanings unless a contrary intention is apparent.

Definitions

In describing and claiming the disclosed subject matter, the following terminology will be used in accordance with the definitions set forth below.

Conductive polymers or, more precisely, intrinsically conducting polymers (ICPs) are organic polymers that conduct electricity. Such compounds may have metallic conductivity or can be semiconductors. Illustrative types of conductive polymers include poly(pyrrole)s, poly(thiophene)s, poly(3,4-ethylenedioxythiophene), polyanilines, poly(acetylene)s, polyphenylene sulfide, poly(p-phenylene vinylene), polyfluorene and their substituted forms (e.g., substituted with one or more halogens).

The term "administration" refers to introducing a composition (e.g., a conductive polymer nanoparticle, a composition including the conductive polymer nanoparticle, or the like) of the present disclosure into a desired location in the subject. In an embodiment, once the composition is administered (e.g., injection) to the desired location of the subject, the composition forms into a gel (e.g., hydrogel) or substance that substantially or completely stays at the location of the administration and is not systemically distributed throughout the body. In an embodiment, administer includes intramuscular, subcutaneous, intradermal, intraarticular, intrathecal, epidural, intracerebral, intraosseous, intraperitoneal, and the like, where the composition is not systemically distributed throughout the body. One preferred route of administration is to administer locally (e.g., directly to the area of interest via a needle or via an incision) so that the composition is not systemically distributed throughout the body.

In accordance with the present disclosure, "an effective amount" of the composition of the present disclosure is defined as an amount sufficient to yield an acceptable outcome (treatment of the condition or disease). In an embodiment, an effective amount of the composition of the present disclosure may be administered in more than one injection and/or stimulation. The effective amount of the compositions of the present disclosure can vary according to factors such as the type of drug, the time frame and amount of released doses, degree of susceptibility of the individual, the age, sex, and weight of the individual, idiosyncratic responses of the individual, the dosimetry, and the like.

As used herein, "treat", "treatment", "treating", and the like refer to acting upon a disease, condition, or disorder with a composition to affect the disease, condition, or disorder by improving or altering it. The improvement or alteration may include an improvement in symptoms or an alteration in the physiologic pathways associated with the disease, condition, or disorder. "Treatment," as used herein, covers one or more treatments of a disease in a host (e.g., a mammal, typically a human or non-human animal of veterinary interest), and includes: (a) reducing the risk of occurrence of the disease, condition, or disorder in a subject determined to be predisposed to the disease but not yet diagnosed as infected with the disease, condition, or disorder, (b) impeding the development of the disease, condition, or disorder, and/or (c) relieving the disease, condition, or disorder, e.g., causing regression of the disease, condition, or disorder and/or relieving one or more disease, condition, or disorder symptoms.

As used herein, the terms "prophylactically treat" or "prophylactically treating" refers completely or partially preventing (e.g., about 50% or more, about 60% or more, about 70% or more, about 80% or more, about 90% or more, about 95% or more, or about 99% or more) a disease, condition, or disorder or symptom thereof and/or may be therapeutic in terms of a partial or complete cure for a disease, condition, or disorder and/or adverse effect attributable to the disease, condition, or disorder.

The term "unit dosage form," as used herein, refers to physically discrete units suitable as unitary dosages for human and/or animal subjects, each unit containing a predetermined quantity of a composition calculated in an amount sufficient (e.g., weight of host, disease, severity of the disease, etc) to produce the desired effect. The specifications for unit dosage forms depend on the particular composition employed, the route and frequency of administration, and the effect to be achieved, and the pharmacodynamics associated with the composition in the host.

The term "therapeutically effective amount" as used herein refers to that amount of an embodiment of the composition being administered that will relieve to some extent one or more of the symptoms of the disease, condition, or disorder being treated, and/or that amount that will prevent, to some extent, one or more of the symptoms of the disease, condition, or disorder that the host being treated has or is at risk of developing.

As used herein, the term "subject" or "host" includes humans and mammals (e.g., mice, rats, pigs, cats, dogs, and horses). Typical subjects to which compounds of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. The term "living subject" refers to host or organisms noted above that are alive. The term "living subject" refers to the entire host or organism and not just a part excised (e.g., a liver or other organ) from the living subject.

Discussion

In accordance with the purpose(s) of the present disclosure, as embodied and broadly described herein, embodiments of the present disclosure, in one aspect, relate to methods of delivering a compound, a composition, and the like.

Embodiments of the present disclosure include methods of controllable and periodically delivering a compound. The delivery can be controlled (rate of dosage) and periodically (e.g., pattern of dosage that can included seconds, minutes, hours, days, weeks) delivered using an electric field. The electric field causes the compound to be delivered. An advantage of the present disclosure is that a subject does not have to be injected with the compound multiple times. Additional details regarding the electric field and delivery of the compound will be described in more detail below and in the Examples.

In an embodiment, the composition including the compound includes a conductive polymer nanoparticle. The conductive polymer nanoparticle can include a conductive polymer encapsulating the compound (e.g., a drug, a biopharmaceutical drug, an imaging agent, and the like), where the compound has a charge associated with it. The encapsulated compound can be released when the conductive polymer nanoparticle is subjected to an electric field. Said differently, the electric field causes the compound to be released from the conductive polymer nanoparticle. Additional details regarding the release of the compound are described in the Examples.

The conductive polymer nanoparticles can be disposed or delivered to an area using a device (e.g., a needle or syringe, or the equivalent of a needle or syringe) or can be disposed in an area during a surgical procedure (e.g., incision, endoscopy, and the like). In an embodiment, the conductive polymer nanoparticles can be localized to a particular area or targeted area (e.g., a tumor, a location of cancer, an injured muscle, ligament, tendon, or bone, location of a medical procedure, and the like). The method can be used to treat pain, treat a disease, condition, and/or disorder, or can be used to deliver an imaging agent. In particular, the conductive polymer nanoparticles can be localized in a particular area using a gel (e.g., hydrogel) or similar material. The targeted area can have an area from a few micrometers cubed to millimeters cubed to centimeters cubed, depending upon the purpose and desired result. Specifically, the conductive polymer nanoparticles can be localized using a temperature sensitive polymer that forms a gel at the body temperature of the subject and can be in a liquid form at temperatures different than the body temperature of the subject. It should be noted that the body temperature of the subject can vary and the targeted area temperature can vary as well, so selection of the temperature sensitive polymer takes these variables into consideration.

Once the composition including the conductive polymer nanoparticles is disposed in a targeted area, an electric field can be applied to the area to controllably release the compound. The electric field can be generated using one or more electrodes disposed adjacent the area, a laser directed towards the area, a microwave, and the like. In an embodiment, the electric field can be about 0.5 to 20 V/cm, about 0.5 to 10 V/cm, or about 0.5 to 2 V/cm, and the bias on the potential can be positive or negative depending on the charge associated with the compound (a positive bias when the charge associated with the compound is positive and vice versa). In an embodiment, the time period for application of the electric field can be about 10 seconds to 3 minutes, for example. The amount of compound to be delivered can be a function of the electric field and the time period of the application of the electric field as well as the constituents of the composition. For example, a larger applied potential can be used to delivery a larger dose of the compound so the time frame for applying the electric field could be reduced, or vice versa. Also, the potential can be applied in a periodic manner (e.g., seconds, minutes, hours, days, weeks) so the applied field and the time period of the applied field can vary depending on the periodic manner in which the compound is to be delivered. So depending upon the circumstances, the electric field and time frame as well as the periodicity can be varied to control the amount of compound delivered. Other variables that may impact the delivery include: the subject, the location of the area, the composition, the compound, the amount of composition, and what the goal is of the delivery of the compound. The delivery of the compound can be tailored based on the particular variables and goals.

As mentioned above, the compound can include a small molecule drug, biopharmaceutical agent, an imaging agent, and the like. The compound can have a charge directly associated with the compound or indirectly associated with the compound so that a normally neutral compound can be used.

One or more compounds can be encapsulated in a conductive polymer. The encapsulation process is described in the Examples. The conductive polymer is biocompatible with the subject. In an embodiment, the types of conductive polymer can include poly(pyrrole)s, poly(thiophene)s, poly(3,4-ethylenedioxythiophene), polyanilines, poly(acetylene)s, polyphenylene sulfide, poly(p-phenylene vinylene), polyfluorene, and their substituted forms (e.g., halogenation, and the like, so long as the conductive polymer functions consistent with the disclosure (e.g., is biocompatible and can used in the encapsulation process)), and a combination thereof. In an embodiment, the conductive polymer nanoparticle can be about 20 to 500 nm in diameter, about 20 to 200 nm in diameter, or about 50 to 100 nm in diameter.

Once the compound(s) is encapsulated in the conductive polymer to form a conductive polymer nanoparticle, an amount (e.g., a therapeutically effective amount in the case of a drug) of the conductive polymer nanoparticles can be selected to be disposed in the subject. As noted above, the conductive polymer nanoparticles can be disposed in one or more ways. A particular embodiment includes the use of a temperature sensitive polymer. In an embodiment, the temperature sensitive polymer can be mixed with the conductive polymer nanoparticles to form a liquid at a temperature that is different than the body temperature of the subject. Since the mixture is a liquid it is easier to administer to the subject. Once disposed in the subject, the temperature sensitive polymer forms a gel, so that conductive polymer nanoparticles are controllable and locally disposed in the area of interest. In an embodiment, the temperature sensitive polymer can include polymers such as (1) diblock or triblock copolymers of poly(ethylene glycol) (PEG) with aliphatic polyesters including polylactide (PLA), polyglycolide (PGA), poly(ε-caprolactone) (PCL), poly[(R)-3-hydroxybutyrate] (PHB); (2) copolymers of poly(ethylene glycol) (PEG) with poly(trimethylene carbonate), poly(propylene fumarate), polyacetal, poly(ethyl-2-cyanoacrylate), poly(amidoamine), or poly(amino urethane); (3) polyphosphazenes, including a hydrophilic poly(ethylene glycol) (PEG) block and hydrophobic amino acids or a peptide block; (4) polypeptides; (5) chitosan and copolymers of chitosan with poly(ethylene glycol) (PEG); (6) poly(ε-caprolactone-co-lactide)-poly(ethylene glycol)-poly-(ε-caprolactone-co-lactide) and its copolymer with acidic sulfamethazine oligomers; (7) copolymers of poly(β-aminoester) with poly(ε-caprolactone) (PCL) and poly(ethylene glycol) (PEG); (8) poly(N-isopropylacrylamide); (9) sulfobetaine-type polymers, and a combination thereof.

At an appropriate time after the conductive polymer nanoparticle is disposed in an area of the subject, the electrical field can be applied to the area for a specific time period to controllably release an amount of the compound. In an embodiment, the electrical field can be applied multiple times at the same or different potential, for the same or different time period, where the multiple times can be on the order of second, minutes, hours, days, or weeks, as needed to obtain the desired result. After a period of time, the remaining conductive polymer and/or other materials disposed in the area can be removed via biological processes.

EXAMPLES

Now having described the embodiments of the present disclosure, in general, the examples describe some additional embodiments of the present disclosure. While embodiments of the present disclosure are described in connection with examples and the corresponding text and figures, there is no intent to limit embodiments of the present disclosure to these descriptions. On the contrary, the intent is to cover all alternatives, modifications, and equivalents included within the spirit and scope of embodiments of the present disclosure.

Example 1

Brief Introduction:

We describe a new temperature and electric field dual-stimulus responsive nanoparticle system for programmed drug delivery. Nanoparticles of a conducting polymer (polypyrrole) are loaded with therapeutic pharmaceuticals and are subcutaneously localized in vivo with the assistance of a temperature-sensitive hydrogel (PLGA-PEG-PLGA). We have shown that drug release from the conductive nanoparticles is controlled by the application of a weak, external DC electric field. This approach represents a novel interactive drug delivery system that can show an externally tailored release profile with an excellent spatial, temporal, and dosage control.

Introduction:

Stimuli-responsive or "smart" biomaterials are of great interest in the fields of biotechnology and biomedicine.[1-5] Many different approaches have been undertaken to cause the response of such a system: stimuli-responsive materials which respond to heat,[6,7] pH,[1,8,9] light,[10-12] enzymes,[13-15] and magnetic field,[16,17] have been used extensively by the biomedical community. Drug delivery systems based on stimulus responsive materials for controlled and long-term drug release under the action of an external stimulus offer the promise of new treatments for chronic diseases that require daily injections or precise doses of medication.

Although many materials that deliver drugs in response to ultrasound, light and magnetic signals have been developed, activating these materials typically requires the use of large or specialized equipment. Electrical signals, on the other hand, are easy to generate and control. Electric stimuli have been successfully utilized to trigger the release of molecules via conducting polymeric bulk materials or implantable electronic delivery devices.[18-20] Abidian et al.[21] prepared the poly(3,4-ethylenedioxythiophene) (PEDOT) coated poly(L-lactide) (PLLA) or poly(lactide-co-glycolide) (PLGA) nanofibers with dexamethasone (Dex) incorporated. After degradation of PLLA or PLGA, the resulted conducting polymer nanotubes provide precisely controlled release of Dex. Wadhwa et al.[22] coated electrodes with polypyrrole (PPy)/Dex films, which allow electric-triggered release of Dex when applying a voltage. Recently, electrically actuatable pulsatile drug release using a polypyrrole-coated nanoporous membrane was reported.[23] Another possibility is to combine light with an electric field, which has been demonstrated for Au nanoparticles.[24]

However, implantable electronic delivery devices often require invasive surgery. In order to bypass the limitations of traditional electric stimuli responsive drug delivery devices, we utilize emulsion polymerization techniques to encapsulate drug compounds in polypyrrole nanoparticles, and develop a new electric field and temperature responsive drug delivery system for triggered and localized release of cargos from these conductive nanoparticles. As shown in FIG. 1.6, the nanoparticles of conducting polymer loaded with a drug serve as a drug reservoir for electric field triggered release. They are suspended in a temperature-responsive hydrogel, which is a liquid at low temperature but becomes a gel at body temperature.[25,26] This mixture can be subcutaneously localized by syringe injection at the place of interest. The application of a small external electric field releases the drug from the nanoparticles and allows the drug to diffuse through the hydrogel to the surroundings.

Nanoparticles have an increased surface area, allowing for a larger amount of drug loading and more sensitive release upon application of an applied electrical field. Our data strongly support our hypothesis that by incorporating conductive nanoparticles within a temperature-sensitive hydrogel we can develop a hybrid "smart" drug delivery system, where in vivo local release of drugs from conductive polymers is firstly successfully achieved in animals. To our knowledge such an in vivo approach has not been previously reported. In addition, the easy combination of conductive nanoparticles within a biodegradable temperature-sensitive hydrogel matrix is minimally invasive and promising for future potential clinical uses.

Results and Discussion
Preparation of the Injectable Conductive Hydrogel:

FIG. 1.1a illustrates the emulsion polymerization of drug-encapsulated polypyrrole (PPy) nanoparticles. This method allows for uniform control of nanoparticle size. In a typical experiment, dodecyltrimethylammonium bromide (DTAB) was selected as a surfactant to form spherical micelles, while decyl alcohol was employed as a cosurfactant to stabilize the emulsion. After introducing the pyrrole monomer into the hydrophobic core of the DTAB/decyl alcohol micelles, ferric chloride as an oxidizing agent was added to initiate the chemical-oxidation polymerization. Two different compounds fluorescein and daunorubicin (FIG. 1.1b shows their chemical structures) were chosen to be loaded into the PPy nanoparticles during the synthesis. Due to the hydrophobicity of these drug compounds, they were localized in the hydrophobic cores of the micelles. After polymerization of pyrrole, polypyrrole nanoparticles were formed with the compounds being encapsulated. And a purification step was applied to remove the surfactants. Fluorescein, a fluorescent probe was used as a drug model for monitoring release. Daunorubicin is a chemotherapeutic agent of the anthracycline family. Both the fluorescein- and daunorubicin-encapsulated polypyrrole nanoparticles have a similar morphology with average diameters of 60 nm (FIG. 1.1d) determined by scanning electron microscopy (SEM), and ~150 nm determined by dynamic light scattering as some aggregates formed in aqueous solution.

The temperature-sensitive polymer poly[(D,L-lactic acid)-co-(glycolic acid)]-b-poly(ethylene oxide)-b-poly[(D, L-lactic acid)-co-(glycolic acid)] (PLGA-PEG-PLGA) which is biocompatible and biodegradable[26] was selected to localize in vivo the PPy nanoparticles at the desired site. The aqueous solution of PLGA-PEG-PLGA exhibits a temperature-responsive sol-gel transition; the critical gelation temperature is dependent on the concentration of the polymer in solution. At lower temperatures the polymer solution is liquid; at higher temperatures (body temperature, 37° C.) the polymer forms a hydrogel. In this study, at 4° C., 0.25 wt % of drug-encapsulated polypyrrole nanoparticles were dispersed in a PBS (pH 7.4) solution containing 25 wt % of PLGA-PEG-PLGA. At 4° C., the temperature-sensitive polymer solution containing PPy nanoparticles could be easily injected through a syringe, while upon exposure at 37° C. the solution phase rapidly underwent transformation to a hydrogel. FIG. 1.1c shows the solidified hydrogels containing PPy nanoparticles at the bottom of a glass bottle as well as on a paper after being injected from a syringe. The SEM image in FIG. 1.1e indicates the relatively uniform distribution of nanoparticles within the hydrogel. Polypyrrole is considered as biocompatible.[27,28] In addition, for following the in vivo study, the PPy nanoparticle sizes were designed to be of 50-100 nm in size allowing for the facile passage and excretion through the circulatory system, after the temperature-sensitive hydrogel fully degrades in vivo.

Release of Drugs in Solution:

The triggered release capabilities of this system were firstly investigated in solution. In phosphate buffered saline (PBS, pH 7.2), a voltage of −0.5 V was applied between two platinum electrodes separated by a distance of 1 cm. The anode was coated with 100 mg of the hydrogel containing 0.25 wt % fluorescein-encapsulated PPy nanoparticles with a thickness around 0.1 cm. The resistivity of the swelled hydrogel and the PBS buffer was measured to be 5400 $\Omega \cdot cm$ and 64 $\Omega \cdot cm$, respectively. Then, the electric field across the hydrogel was calculated to be approximately −4.5 V/cm. The electrical stimulus was applied for 10 seconds, which was repeated every five minutes, followed by measurements of the concentration of free fluorescein in the solution. FIG. 1.2a shows that over a 30 minute period, fluorescein was released stepwise upon application of the electric field across the hydrogel. For each stimulus, ~20 ng of fluorescein was released. The voltage between the two electrodes was then set at −1.5 V (corresponding to an electric field across the hydrogel of −13.6 V/cm). At this higher voltage, as shown in FIG. 1.2a, ~60 ng of fluorescein was released during the first stimulus; while upon each subsequent stimuli ~30 ng of fluorescein was released. The higher amount observed during the first stimulus may result from higher drug loading within the nanoparticles. Our interest in the practicability of this triggered release led us to perform a long-term release study over seven days. With the voltage between the two electrodes at −1.0 V (corresponding to an electric field across the hydrogel of −9.0 V/cm), the pulsed electric stimulus was applied to the conductive hydrogels for 20 s, once every 24 hr, followed by concentration measurements of free fluorescein in solution. FIG. 2b shows that approximately 60 ng of fluorescein was released each day upon electric stimulus. As a control, no obvious release of fluorescein was detected without applying voltage. In the case of daunorubicin, an electric field across the hydrogel of 4.5 V/cm (the set voltage was 0.5 V) was applied for 10 seconds every 5 minutes. As shown in FIG. 1.2c, upon each stimulus, ~25 ng of daunorubicin was released into solution.

By applying voltage until no obvious drug release could be detected, the loading percentage of fluorescein and daunorubicin in PPy nanoparticles was calculated to be around 3.6 wt % and 3.2 wt %. Comparing to sustained release of fluorescein and daunorubicin in hydrogel without encapsulating them in PPy nanoparticles (FIG. 1.2d shows most of the drugs in hydrogel were released in 4 days), no obvious release of encapsulated fluorescein or daunorubicin from PPy nanoparticles in hydrogel was detected without applying an electric field. This behavior indicates that encapsulation of drugs in PPy nanoparticles prevents the undesired release from the hydrogel. Only with an electric stimulus can drugs be released on command. This represents an important advantage of our delivery system over conventional sustained release of drugs from hydrogel. By comparing the above release studies, we have demonstrated that the released dose of the drug could be roughly controlled by either the strength of the electric field or the duration time of the electric field.

Mechanism of Electric Field Triggered Release:

The electric field triggered release possibly involves a synergistic process of electrochemical reduction/oxidation and electric-field-driven movement of charged molecules. In our work, either negatively charged fluorescein or positively charged daunorubicin molecules were incorporated into PPy nanoparticles during the chemical synthesis. The release of molecules by electrochemical reduction/oxidation process is known for PPy bulk materials.[20-22] Similar to that, in our study, upon reduction, fluorescein was released from the PPy nanoparticles, while daunorubicin was released upon oxidation. Release of the drug is directly related to the change of the overall net charge within the polymer nanoparticles upon reduction or oxidation, which is known to cause conformational change; as the charge density of the PPy nanoparticles changes the contraction of the nanoparticles and repulsion of noncovalently bonded drug molecules occurs. Upon reduction, the positive charge within the polypyrrole nanoparticles is reduced, expelling fluorescein molecules from the nanoparticles and causing net overall contraction of the nanoparticles. Upon oxidation, the positive charge within the polypyrrole nanoparticles is increased, which leads to repulsion of the positively charged daunorubicin molecules. After molecules are released from PPy nanoparticles by the electrochemical reduction/oxidation process, electric-field-driven migration plays an important role in the movement of charged entities toward the electrode bearing an opposite charge, which resulted in the escape of drugs from the hydrogel. The morphology of the fluorescein-encapsulated polypyrrole nanoparticles after release was shown by SEM images in FIG. 1.3. For the release experiment, the anode was coated with 20 mg of the hydrogel containing 0.25 wt % fluorescein-encapsulated PPy nanoparticles. Then a voltage of −1.5 V between the two electrodes (corresponding to an electric field across the hydrogel of −13.6 V/cm) was applied for 60 seconds, which was repeated every 20 minutes. Compared to the uniform and spherical nanoparticles before release, after release most of the nanoparticles lost their uniform and spherical shapes and appeared more shrinked in size. By recording the sizes of nanoparticles from SEM images, the shrinkage of the nanoparticles was roughly calculated to be 17.2% in diameter and thus 43.3% in volume. Ab initio calculations[29] show that a neutral polypyrrole chain in the ground state assumes a helical shape resulting from a novel bending mechanism, while upon oxidation the chain becomes planar, an effect attributed to enhanced inter-ring bonding.

Biocompatibility of the Conductive Hydrogel:

To confirm the biocompatibility of the conductive hydrogel in mice, the solution containing PLGA-PEG-PLGA and 1 wt % of PPy nanoparticles were subcutaneously injected at dorsal sites of FVB adult mice (FIGS. 1.4a and 1.4b). Once injected, the solution solidifies into hydrogel immediately at body temperature. Histological observation of hydrogel have been carried out after H&E staining and represented in FIGS. 1.4c and 1.4d. The initial thermo-responsive hydrogel has no infiltrated cells. Various types of cells are observed to be in the hydrogel at 7 and 14 days after injection (FIGS. 1.4c and 1.4d). The implanted hydrogel containing high concentrations of PPy NPs (>5 wt %) were observed to be encapsulated by fibrous tissue and covered with a regenerated thick pleura-like cell membrane after 2 weeks. The hydrogel containing an optimal concentration of PPy NPs (1 wt %) did not exhibit any fibrous tissue encapsulation as shown in FIGS. 1.4a and 1.4b. H&E staining showed that the skin layers were structurally clear and no infiltration by neutrophilic granulocytes and lymphocytes were found at days 7 and 14 (FIGS. 1.4c and 1.4d). Histologically, no obvious differences were observed between the experimental group and the control group. This result is consistent with previous reports on biocompatibility of PPy nanoparticles[27,28,30,31] and PLGA-PEG-PLGA hydrogel[26] in vivo.

Electric Field Triggered Release In Vivo:

For in vivo release studies, 200 µL of fluorescein-encapsulated polypyrrole nanoparticles (1 wt %) dispersed in PBS (pH 7.2) (25 wt % PLGA-PEG-PLGA) was injected at two distinct dorsal sites of FVB adult mice. An electric field of −1.5 V/cm was applied for 40 s onto one of injection sites (left site in FIG. 1.5) during each stimulus, while the other injection site (right site in FIG. 1.5) was set as a control without applying voltage. The triggered release of fluorescein was monitored by in vivo fluorescent imaging, and the increased fluorescence in the region of interest was quantified (FIG. 1.5). After each stimulus, the release of fluorescein was observed, while as a comparison no obvious release of fluorescein was detected without applying electric field. A doubling of the increase in the fluorescence signal occurred for the second stimulus. We suggest that this increase is caused by release of fluorescent molecules in the hydrogel combined with new release of fluorescent molecules from the PPy nanoparticles. Rapid monitoring of the fluorescence arising from the released molecules provides a unique platform to optimize and develop the electric field responsive drug release.

One can envision clinical applications of this controlled release system for pain relief which needs a given dosage at desired periodical time by applying a weak external voltage from a small battery on the subcutaneously implanted hydrogel, and for anticancer therapy in which case the tumor cannot be easily removed by a surgery. One can also envision clinical application for the programmed drug delivery that is coupled to presence of weak electric fields in vivo. Specifically, tissues with naturally occurring electric fields can couple substance release and drug delivery to electrical activity within the tissue.

In cardiovascular tissue engineering intrinsic electrical activity of the pacemaker cells (sinoatrial node) can cause specific encapsulated substance to be released rhythmically with each pulse. Alternatively, transvenously inserted pacemakers can be programmed to generate electrical activity and thus programmed substance release to induce various desired responses such as stem cell homing, anti-apoptotic activity, or pro-angiogenic stimulus. Similarly, neuronal tissue with intrinsic weak electric fields can stimulate particular neurotransmitter release enclosed within the nanoparticles that is coupled with electrical activity within regions of the brain.

Conclusions

In summary, we have demonstrated that a dual-stimulus (temperature and electric field) responsive system containing nanoparticles made of the conducting polymer polypyrrole can be used to trigger sensitive dosage-controlled release of drugs. This approach is facile and minimally invasive for potential medical application. It represents a new electric field responsive drug delivery system that we suggest has excellent spatial and temporal control.

Materials and Methods

Materials:

Pyrrole (Py), dodecyltrimethylammonium bromide (DTAB), decyl alcohol, ferric chloride, fluorescein, and daunorubicin were purchased from Sigma-Aldrich. Poly[(D, L-lactic acid)-co-(glycolic acid)]-b-poly(ethylene oxide)-b-poly[(D,L-lactic acid)-co-(glycolic acid)] (PLGA-PEG- PLGA) ((molecular weight: 1500:1000:1500) was from Akina, Inc., West Lafayette, Ind. Poly(styrenesulfonic acid), sodium salt (PSS-Na+) (molecular weight: 500000) was from Polysciences, Inc., Warrington, Pa.

Synthesis of Polypyrrole Nanoparticles and Drug Encapsulation:

DTAB and decyl alcohol were added to deionized water at concentrations of 50 mg/mL and 37.5 mg/mL, respectively at 4° C. Then, pyrrole and fluorescein (or daunorubicin) were added to the emulsion to reach a concentration of 6.25 mg/mL and 0.6 mg/mL. For encapsulation of daunorubicin, 2 mg/mL of PSS$^-$Na$^+$ was added to the above emulsion to serve as counter-ions that incorporate positively charged daunorubicin in the nanoparticles. Then, ferric chloride aqueous solution (0.07 g/mL) was added to the above emulsion, followed by stirring at 4° C. for 2 h until completion. After the reaction, the product was precipitated out, washed with ethanol to remove DTAB and collected by centrifugation. We find that ~37.5% of fluorescein and ~33.3% of daunorubicin are incorporated into the PPY nanoparticles, based on the drug to pyrrole feed ratio in the emulsion polymerization.

Release Study in Solution:

The platinum anode was firstly coated with the PLGA-PEG-PLGA polymer solution (100 mg of polymer) containing 0.25 wt % fluorescein (or daunorubicin)-encapsulated PPy nanoparticles, followed by solidification of the gel at room temperature. The PPy nanoparticles in the solidified gel was calculated to be 1 wt %. The coated platinum anode was then immersed in phosphate buffered saline (PBS, pH 7.2) together with a counter platinum electrode with a separated distance of 1 cm. For the release study in solution, specific voltages were applied between the two electrodes, followed by measurements of the concentration of released molecules by fluorescent assays.

Scanning Electron Microscopy (SEM) Measurement:

SEM images were acquired using an FEI XL30 Sirion SEM with FEG source and EDX detector. Dry samples (dry PPy nanoparticles and air-dried hydrogel containing PPy nanoparticles) on carbon sticky tapes were observed directly under SEM.

In Vivo Biocompatibility:

For testing the biocompatibility of hydrogel containing PPy nanoparticles in vivo, 100 µL of PLGA-PEG-PLGA PBS (pH 7.4) solution (25 wt % of polymer) containing 0.25 wt % of PPy nanoparticles (sterilized under LTV radiation for 2 hours) were subcutaneously injected by a syringe at dorsal sites of adult female FVB mice (10 weeks old) purchased from Charles River Laboratories (Wilmington, Mass.). The PPy nanoparticles in the solidified gel was calculated to be 1 wt %. Histological examination was performed to observe the cell growth within the conductive hydrogel and to predict the biodegradation procedure of the conductive hydrogel. All mice were sacrificed and the implants were individually dissected and removed from the subcutaneous dorsum at 1 and 2 weeks after implantation. The specimens were immediately fixed in 4% paraformaldehyde, dehydrated, and embedded in paraffin blocks. The embedded specimens were sectioned (5 µm thick) along the longitudinal axis of the implant. Slides were stained by hematoxylin and eosin (H&E).

In Vivo Release:

For in vivo release, a patch of hair was removed from the dorsal side of FVB adult female mice (10 weeks old) with hair clippers; Nair depilatory cream (Church and Dwight) was applied for 60 s and then wiped and washed off. At 4° C. 0.25 wt % of fluorescein-encapsulated polypyrrole nanoparticles were dispersed in PBS (pH 7.2) containing 25 wt % of PLGA-PEG-PLGA. For each mouse, 200 µL of the above conductive hydrogel was subcutaneously injected at two separate dorsal sites. The PPy nanoparticles in the solidified gel was calculated to be 1 wt %. An electric field of −1.5 V/cm was applied onto the implanted gels for 40 s per each stimulus via two needle electrodes. Fluorescent imaging was performed using an in vivo imaging system (Xenogen Corporation, Alameda, Calif.). For quantification, a region of interest (ROI) was manually selected based on the signal intensity. The area of ROI was kept constant and the intensity was recorded as average photons per second per square centimeter per steridian.

References, each of which is incorporated herein by reference.

1. Anderson, D.; Burdick, J.; Langer, R. Smart Biomaterials. *Science* 2004, 305, 1923-1924.
2. Stuart, M. A. C.; Huck, W. T. S.; Genzer, J.; Muller, M.; Ober, C.; Stamm, M.; Sukhorukov, G. B.; Szleifer, I.; Tsukruk, V. V.; Urban, M.; et al. Emerging Applications of Stimuli-Responsive Polymer Materials. *Nat. Mater.* 2010, 9, 101-113.
3. Guo, X.; Szoka, F. C. Chemical Approaches to Triggerable Lipid Vesicles for Drug and Gene Delivery. *Acc. Chem. Res.* 2003, 36, 335-341.
4. LaVan, D. A.; McGuire, T.; Langer, R. Small-Scale Systems for in vivo Drug Deliver. *Nat. Biotechnol.* 2003, 21, 1184-1191.
5. Grayson, A. C. R.; Choi, I. S.; Tyler, B. M.; Wang, P. P.; Brem, H.; Cima, M. J.; Langer, R. Multi-Pulse Drug Delivery from a Resorbable Polymeric Microchip Device. *Nat. Mater.* 2003, 2, 767-772.
6. Yavuz, M. S.; Cheng, Y.; Chen, J.; Cobley, C. M.; Zhang, Q.; Rycenga, M.; Xie, J.; Kim, C.; Song, K. H.; Schwartz, A. G.; et al. Gold Nanocages Covered by Smart Polymers for Controlled Release with Near-Infrared Light. *Nat. Mater.* 2009, 8, 935-939.
7. Choi, S. W.; Zhang, Y.; Xia, Y. A Temperature-Sensitive Drug Release System Based on Phase-Change Materials. *Angew. Chem. Int. Ed.* 2010, 49, 7904-7908.
8. Gillies, E. R.; Jonsson, T. B.; Frechet, J. M. J. Stimuli-Responsive Supramolecular Assemblies of Linear-Dendritic Copolymers. *J. Am. Chem. Soc.* 2004, 126, 11936-11943.
9. Kim, K. T.; Cornelissen, K. J. J. L. M.; Nolte, R. J. M.; van Hest, J. C. M. A Polymersome Nanoreactor with Controllable Permeability Induced by Stimuli-Responsive Block Copolymers. *Adv. Mater.* 2009, 21, 2787-2791.
10. Kostiainen, M. A.; Kasyutich, O.; Cornelissen, J. J. L. M.; Nolte, R. J. M. Self-Assembly and Optically Triggered Disassembly of Hierarchical Dendron-Virus Complexes. *Nat. Chem.* 2010, 2, 394-399.
11. Dvir, T.; Banghart, M. R.; Timko, B. P.; Langer, R.; Kohane, D. S. Photo-Targeted Nanoparticles. *Nano Lett.* 2010, 10, 250-254.
12. Chakravarty, P.; Qian, W.; EI-Sayed, M. A.; Prausnitz, M. R. Delivery of Molecules into Cells Using Carbon Nanoparticles Activated by Femtosecond Laser Pulses. *Nat. Nanotechnol.* 2010, 5, 607-611.
13. Azagarsamy, M. A.; Sokkalingam, P.; Thayumanavan, S. Enzyme-Triggered Disassembly of Dendrimer-Based Amphiphilic Nanocontainers. *J. Am. Chem. Soc.* 2009, 131, 14184-14185.
14. Thornton, P. D.; Heise, A. Highly Specific Dual Enzyme-Mediated Payload Release from Peptide-Coated Silica Particles. *J. Am. Chem. Soc.* 2010, 132, 2024-2028.

15. Ge, J.; Lu, D.; Yang, C.; Liu, Z. A Lipase-Responsive Vehicle Using Amphipathic Polymer Synthesized with the Lipase as Catalyst. *Macromol. Rapid Commun.* 2011, 32, 546-550.
16. Namiki, Y.; Namiki, T.; Yoshida, H.; Ishii, Y.; Tsubota, A.; Koido, S.; Nariai, K.; Mitsunaga, M.; Yanagisawa, S.; Kashiwagi, H.; et al. A Novel Magnetic Crystal-Lipid Nanostructure for Magnetically Guided in vivo Gene Delivery. *Nat. Nanotechnol.* 2009, 4, 598-606.
17. Dames, P.; Gleich, B.; Flemmer, A.; Hajek, K.; Seidl, N.; Wiekhorst, F.; Eberbeck, D.; Bittmann, I.; Bergemann, C.; Weyh, T.; et al. Targeted Delivery of Magnetic Aerosol Droplets to the Lung. *Nat. Nanotechnol.* 2007, 2, 495-499.
18. Simon, D. T.; Kurup, S.; Larsson, K. C.; Hori, R.; Tybrandt, K.; Goiny, M.; Jager, E. W.; Berggren, M.; Canton, B.; Richter-Dahlfors, A. Organic Electronics for Precise Delivery of Neurotransmitters to Modulate Mammalian Sensory Function. *Nat. Mater.* 2009, 8, 742-746.
19. George, P. M.; LaVan, D. A.; Burdick, J. A.; Chen, C.-Y.; Liang, E.; Langer, R. Electrically Controlled Drug Delivery from Biotin-Doped Conductive Polypyrrole. *Adv. Mater.* 2006, 18, 577-581.
20. Svirskis, D.; Travas-Sejdic, J.; Rodgers, A.; Garg, S. Electrochemically Controlled Drug Delivery Based on Intrinsically Conducting Polymers. *J. Controlled Release* 2010, 146, 6-15.
21. Abidian, M. R.; Kim, D. H.; Martin, D. C. Conducting-Polymer Nanotubes for Controlled Drug Release. *Adv. Mater.* 2006, 18, 405-409.
22. Wadhwa, R.; Lagenaur, C. F.; Cui, X. T. Electrochemically Controlled Release of Dexamethasone from Conducting Polymer Polypyrrole Coated Electrode. *J. Controlled Release* 2006, 110, 531-541.
23. Jeon, G.; Yang, S. Y.; Byun, J.; Kim, J. K. Electrically Actuatable Smart Nanoporous Membrane for Pulsatile Drug Release. *Nano Lett.* 2011, 11, 1284-1288.
24. Balogh, D.; Tel-Vered, R.; Freeman, R.; Willner, I. Photochemically and Electrochemically Triggered Au Nanoparticles "Sponges". *J. Am. Chem. Soc.* 2011, 133, 6533-6536.
25. Jeong, B.; Bae, Y. H.; Lee, D. S.; Kim, S. W. Biodegradable Block Copolymers as Injectable Drug Delivery Systems. *Nature* 2007, 388, 860-862.
26. Yu, L.; Zhang, Z.; Zhang, H.; Ding, J. Biodegradability and Biocompatibility of Thermoreversible Hydrogels Formed from Mixing a Sol and Ap of Block Copolymers in Water. *Biomacromolecules* 2010, 11, 2169-2178.
27. George, P. M.; Lyckman, A. W.; LaVan, D. A.; Hegde, A.; Leung, Y.; Avasare, R.; Testa, C.; Alexander, P. M.; Langer, R.; Sur, M. Fabrication and Biocompatibility of Polypyrrole Implants Suitable for Neural Prosthetics. *Biomaterials* 2005, 26, 3511-3519.
28. Ramanaviciene, A.; Kausaite, A.; Tautkus, S.; Ramanavicius, A. Biocompatibility of Polypyrrole Particles: an in-vivo Study in Mice. *J. Pharm. Pharmocol.* 2007, 59, 311-315.
29. Lin, X. Li, J.; Smela, E.; Yip, S. Polaron-Induced Conformation Change in Single Polypyrrole Chain: An Intrinsic Actuation Mechanism. *Int. J. Quantum Chem.* 2005, 102, 980-985.
30. Wang, Z.; Roberge, C.; Dao, L. H.; Wan, Y.; Shi, G.; Rouabhia, M.; Guidoin, R.; Zhang, Z. In vivo Evaluation of a Novel Electrically Conductive Polypyrrole/poly(D, L-lactide) Composite and Polypyrrole-Coated Poly(D,L-lactide-co-glycolide) Membranes. *J. Biomed. Mater. Res., Part A* 2004, 70A, 28-38.
31. Jiang, X.; Marois, Y. Traoré, A.; Tessier, D. Dao, L. H.; Guidoin, R.; Zhang, Z. Tissue Reaction to Polypyrrole-Coated Polyester Fabrics: an in vivo Study in Rats. *Tissue Engineering* 2002, 8, 635-647.

Example 2

D-Luciferin-Encapsulated Polypyrrole Nanoparticles for Electric Field-Triggered Release Dodecyltrimethylammonium bromide (DTAB) and decyl alcohol were added to 40 mL of deionized water at a concentration of 50 mg/mL and 37.5 mg/mL, respectively, followed by stirring at 4° C. for 10 min. Pyrrole and D-luciferin was added to the emulsion to reach a concentration of 6.25 mg/mL and 2.5 mg/mL, respectively, followed by stirring at 4° C. for 10 min to form an emulsion. Then, 1 mL of ferric chloride aqueous solution (2.8 g/mL) was added to the above emulsion, followed by stirring at 4° C. for 2 h to conduct the reaction. After reaction, the product was precipitated in and washed with 400 mL of ethanol and collected by centrifugation. This process was repeated twice. Finally, black powdery product was dried at room temperature under vacuum for 24 h.

D-luciferin-encapsulated polypyrrole nanoparticles were synthesized the by an emulsion polymerization which could control the sizes of the nanoparticles. Luciferin served as a model molecule was incorporated in the polymer nanoparticle. As shown in the scanning electron microscopy (SEM) images (FIG. 2.1), the luciferin encapsulated polypyrrole nanoparticles have the average diameter of 70 nm. At 4° C., 0.05 wt % of polypyrrole nanoparticles were dispersed in the water solution containing 15 wt % of poly[(D,L-lactic acid)-co-(glycolic acid)]-b-poly(ethylene oxide)-b-poly[(D, L-lactic acid)-co-(glycolic acid)] (PLGA-PEG-PLGA). After exposed to 37° C., the solution becomes a hydrogel immediately. The SEM images (FIG. 2.2) of the morphology of dried hydrogel containing nanoparticles show the distribution of nanoparticles inside the gel.

An electrical stimulus of −2.0 V/cm was applied for 10 seconds on the platinum electrodes in every 5 minutes, followed by measuring the concentration of luciferin in the solution. As shown in FIG. 2.3, luciferin was released by applying the electric stimulus. The control experiment without applying voltage shows no release of the molecules.

Example 3

Fluorescein-Encapsulated Poly(3,4-Ethylenedioxythiophene) Nanoparticles for Electric Field-Triggered Release Fluorescein-encapsulated poly(3,4-ethylenedioxythiophene) (PEDOT) nanoparticles were synthesized the by an emulsion polymerization which could control the sizes of the nanoparticles. Fluorescein served as a model molecule was incorporated in the polymer nanoparticle. As shown in the scanning electron microscopy (SEM) images (FIG. 3.1), the fluorescein encapsulated PEDOT nanoparticles have the average diameter of 45 nm. At 4° C., 2 wt % of polypyrrole nanoparticles were dispersed in the water solution containing 40 wt % of poly[(D,L-lactic acid)-co-(glycolic acid)]-b-poly(ethylene oxide)-b-poly[(D,L-lactic acid)-co-(glycolic acid)] (PLGA-PEG-PLGA). After exposed to 37° C., the solution becomes a hydrogel immediately. The SEM images (FIG. 3.2) of the morphology of dried hydrogel containing nanoparticles show the distribution of nanoparticles inside the gel.

An electrical stimulus of −1.0 V/cm was applied for 10 seconds on the platinum electrodes in every 5 minutes, followed by measuring the concentration of fluorescein in the solution. By measuring the concentration of fluorescein in the solution, the amount of the fluorescein molecules released out from the PEDOT nanoparticles upon each stimulus was determined. In a period of 30 minutes, as shown in FIG. 3.3, fluorescein was released step by step by applying the electric stimulus. The control experiment without applying voltage shows no release of the molecules.

Example 4

Fluorescein-Encapsulated Polypyrrole Nanoparticles for Electric Field-Triggered Release with Cells For in vitro study, at 4° C., 1 wt % of fluorescein-encapsulated polypyrrole nanoparticles were dispersed in the phosphate buffered saline (PBS) solution containing 20 wt % of poly[(D,L-lactic acid)-co-(glycolic acid)]-b-poly (ethylene oxide)-b-poly[(D,L-lactic acid)-co-(glycolic acid)] (PLGA-PEG-PLGA). The solution was then mixed with cardiac progenitor cells in cell culture at 4° C. 200 µL of the above solution was added to each well of a 96 well plate and solidified at 37° C. for 10 min, followed by applying voltage on the hydrogel for 1 minute using platinum wires. Then 100 µL of supernatant phosphate buffered saline (PBS) was taken out to determine the amount of the fluorescein released upon the electrical stimulus. As shown in FIG. 4.1, a voltage of −0.085 V/cm (sample 1) is not enough to trigger the release of encapsulated fluorescein in conductive nanoparticles, while a voltage of −0.5 V/cm (sample 2) can trigger the release. As a control (sample 3), there is no release of fluorescein without applying voltage. As another control, there is no fluorescent intensity increase when applying −0.5 V/cm voltage on conductive nanoparticles without fluorescein.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to what is being measured. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

We claim:

1. A method of delivering a composition, comprising:
disposing a composition including a conductive polymer nanoparticle into an area of a subject, wherein the conductive polymer nanoparticle includes a conductive polymer encapsulating a compound, wherein a charge is associated with the compound; and
applying an electric field to the area for a period of time, wherein the electric field causes the controllable release of the compound from the conductive polymer nanoparticle.

2. The method of claim 1, further comprising repeating the step of applying the electric field in a periodic manner over the course of seconds to weeks.

3. The method of claim 1, wherein the compound is a drug compound.

4. The method of claim 1, wherein the conductive polymer nanoparticle is included in a mixture of a temperature sensitive polymer, wherein the temperature sensitive polymer forms a gel when at the body temperature of the subject, wherein use of the temperature sensitive polymer permits localization of the conductive polymer nanoparticle so that the compound is released locally to the area it was disposed in.

5. The method of claim 1, wherein a bias of the electric field is determined by the charge associated with the compound.

6. The method of claim 5, wherein the electric field is generated by applying a potential of about 0.5 to 20 volts per centimeter.

7. The method of claim 1, wherein the time frame of the applied electric field is about 10 seconds to 2 minutes.

8. The method of claim 1, wherein the electric field and the time frame of the electric field determine the amount of compound released.

9. The method of claim 1, wherein the electric field is generated using one of the following: a pair of electrode contacts, a laser, a microwave generating apparatus, and ultrasound.

10. The method of claim 1, wherein disposing includes locally administering to the area so that the composition is not systemically distributed throughout the body.

11. The method of claim 10, wherein locally administering includes administering the composition using a needle.

12. The method of claim 11, wherein locally administering includes an injection type selected from the group consisting of: intramuscular, subcutaneous, intradermal, intraarticular, and intrathecal.

13. The method of claim 12, wherein the conductive polymer nanoparticle is included in a mixture of a temperature sensitive polymer, wherein the temperature sensitive polymer forms a gel when at the body temperature of the subject, wherein use of the temperature sensitive polymer permits localization of the conductive polymer nanoparticle.

14. The method of claim 13, wherein the conductive polymer is selected from poly(pyrrole)s, poly(thiophene)s, poly(3,4-ethylenedioxythiophene), polyanilines, poly(acetylene)s, polyphenylene sulfide, poly(p-phenylene vinylene), polyfluorene and their substituted forms, and a combination thereof.

15. The method of claim 14, wherein the temperature sensitive polymer is selected from: diblock or triblock copolymers of poly(ethylene glycol) (PEG) with aliphatic polyesters including polylactide (PLA), polyglycolide (PGA), poly(ε-caprolactone) (PCL), poly[(R)-3-hydroxybutyrate] (PHB); copolymers of poly(ethylene glycol) (PEG) with poly(trimethylene carbonate), poly(propylene fumarate), polyacetal, poly(ethyl-2-cyanoacrylate), poly(amidoamine), or poly(amino urethane); polyphosphazenes, consisting of a hydrophilic poly(ethylene glycol) (PEG) block and hydrophobic amino acids or a peptide block; polypeptides; chitosan and copolymers of chitosan with poly(ethylene glycol) (PEG); poly(ε-caprolactone-co-lactide)-poly(ethylene glycol)-poly-(ε-caprolactone-co-lactide) and its copolymer with acidic sulfamethazine oligomers; copolymers of poly(β-aminoester) with poly(ε-caprolactone) (PCL) and poly(ethylene glycol) (PEG); poly(N-isopropylacrylamide); sulfobetaine-type polymers and a combination thereof.

16. The method of claim 1, wherein applying an electric field includes applying the electric field using a device.

* * * * *